United States Patent [19]

Warriner

[11] Patent Number: Plant 5,639

[45] Date of Patent: Jan. 21, 1986

[54] ROSE PLANT JACANGE 74-3563

[75] Inventor: William A. Warriner, Tustin, Calif.

[73] Assignee: Jackson & Perkins Company, Medford, Oreg.

[21] Appl. No.: 596,827

[22] Filed: Apr. 4, 1984

[51] Int. Cl.[4] ..... A01H 5/00

[52] U.S. Cl. ..... Plt./17

[58] Field of Search ..... Plt./17

*Primary Examiner*—Robert E. Bagwill

*Attorney, Agent, or Firm*—Klarquist, Sparkman, Campbell, Leigh & Whinston

[57] ABSTRACT

A hybrid tea rose variety having an upright plant similar in habit to the seed parent, flower color very close to R.H.S. 33A and then changing to R.H.S. 42C after a few days, numerous prickles, little or no fragrance, and very good resistance to rose powdery mildew.

1 Drawing Figure

1

This present invention relates to a new and distinct variety of rose plant of the hybrid tea class which was originated by me by crossing the variety Apricot Parfait, non-patented, with the variety Futura, U.S. Plant Pat. No. 3,569.

The primary object of this breeding was to produce a new rose variety combining the colors, mildew resistance, and other characteristics of Futura with the more erect and stiff stems of Apricot Parfait. This objective was substantially achieved along with other desirable improvements as evidenced by the following unique combination of characteristics which are outstanding in the new variety and which distinguish it from its parents, as well as from all other varieties of which I am aware:

1. An upright plant similar in habit to the seed parent, Apricot Parfait.
2. Flower color very close to R.H.S. 33A, changing to R.H.S. 42C after three or four days.
3. Numerous prickles, hooked downward and numerous small prickles.
4. Little or no fragrance.
5. Very good resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Apricot Parfait, non-patented.

*Pollen parent.*—Futura, U.S. Plant Pat. No. 3,569.

Classification:

*Botanical.*—Rosa hybrid.

*Commercial.*—Hybrid tea.

2

FLOWER

Observations made from specimens grown at Irvine, Calif. in November.

Blooming habit: Continuous.

Bud:

*Size.*—1" to 1¼" when petals start to unfurl.

*Form.*—Blunt top.

*Color.*—When sepals first divide, mostly Red Group 33A, being lighter near base of petals. When half blown; upper side of petals Red Group 33A; lower side of petals Red Group 33A.

*Sepals.*—Color: Outer surface Green 138A with glandular texture. Three appendaged sepals lightly appendaged. Two unappendaged sepals hairy edged.

*Receptacle.*—Color: Green 138A. Shape: Funnel. Size: Large, broad. Surface: Glandular.

*Peduncle.*—Length: Short. Surface: Glandular. Color: Light green. Strength: Stiff, erect.

*Opening.*—Petals fold outward without quilling.

Bloom:

*Size.*—Medium. Average open size: 4" to 4½".

*Borne.*—Singly.

*Stems.*—Medium, strong.

*Form.*—When first open, high center. Permanence: Flattens.

*Petalage.*—Number of petals under normal conditions: 35–40.

*Color.*—Center of flower: Upper side of petals Red Group 33A; reverse side of petals Red Group 33A; base of petals have pale yellow area at point of attachment. General tonality from a distance: Orange equivalent to R.H.S. Red Group 33A.

*Variegations.*—Weather streaks on outer petals.

*Discoloration.*—General tonality at end of first day: No change. Third day: Lighter orange equivalent to R.H.S. Red 42C.

*Fragrance.*—None.

Petals:

*Texture.*—Thin.

*Shape.*—Round.

*Form.*—Nearly flat.

*Arrangement.*—Imbricated. Petaloids in center: few.

*Persistence.*—Drop off cleanly.

*Lastingness.*—On the plant, long. As cut flower, long.

Reproductive parts:

*Anthers.*—Medium, many. Color: Yellow. Arrangement: Regular around styles.

*Filaments.*—Color: Yellow.

*Styles.*—Color: Greenish-white.

*Stigmas.*—Color: Greenish-white.

PLANT

Form: Bush.

Growth: Vigorous, upright.

Foliage: Number of leaflets on normal mid-stem leaves: 5 or 7.

*Size.*—Large.

*Quantity.*—Normal.

*Color.*—New foliage: Near greyed purple 187A. Old foliage: Dark green above light green on lower sides.

Leaflets:

*Shape.*—Broadly oval.

*Texture.*—Leathery on upper side.

*Edge.*—Serrated.

*Serration.*—Single, small.

*Petiole.*—Rachis: Color: Green.

*Stipules.*—Medium, bearded.

*Disease resistance.*—Resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base: Many. On laterals from stalk: Many.

*Form.*—Hooked downward.

*Color when young.*—Brown.

*Position.*—Irregular.

Small prickles:

*Quantity.*—On main stalks: Many. On laterals: Many.

*Color.*—Brown.

I claim:

1. A new and distinct variety of rose plant of the hybrid tea class, substantially as herein shown and described, characterized particularly as to novelty by the unique combination of its upright plant whose foliage is resistant to rose powdery mildew, stems which bear both large and small prickles, and whose blooms are orange (R.H.S. 33A) and lacking in fragrance.

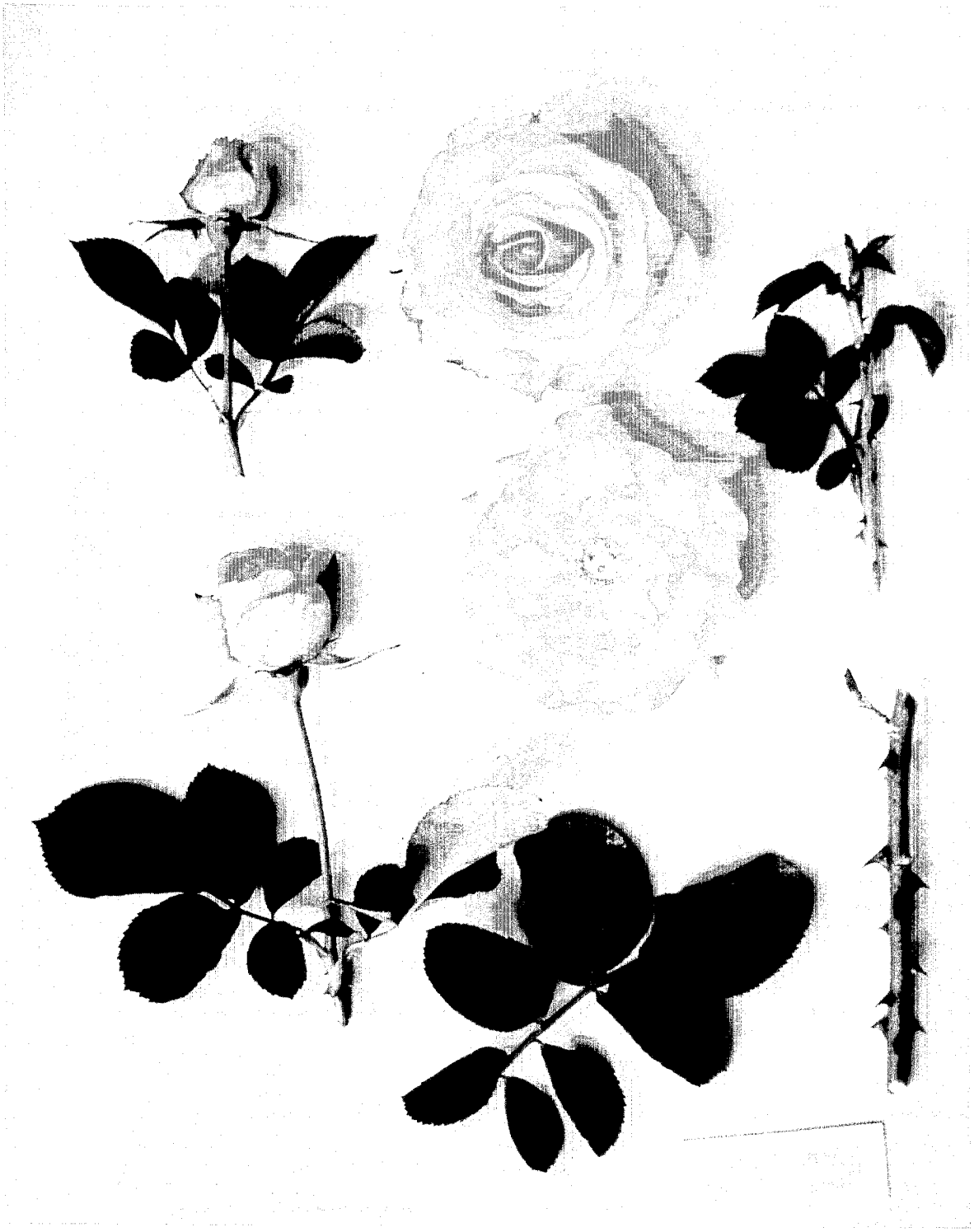

* * * * *